United States Patent [19] [11] 3,967,494
Joslyn [45] July 6, 1976

[54] METHOD AND APPARATUS FOR DETECTING ENTRAPPED AIR IN A STEAM STERILIZER

[75] Inventor: Larry James Joslyn, Walworth, N.Y.

[73] Assignee: Sybron Corporation, Rochester, N.Y.

[22] Filed: Feb. 28, 1975

[21] Appl. No.: 553,974

[52] U.S. Cl. .................................. 73/29; 21/56; 21/94; 21/103; 21/104; 23/253 A
[51] Int. Cl.² .................. A61L 1/00; A61L 3/02; G01N 7/14
[58] Field of Search ............... 21/103, 104, 94–98, 21/56; 73/29

[56] References Cited
UNITED STATES PATENTS

| | | | |
|---|---|---|---|
| 2,112,639 | 3/1938 | Underwood | 21/104 UX |
| 3,002,372 | 10/1961 | Bulkley et al. | 73/29 |
| 3,431,065 | 3/1969 | Schipanski | 21/94 X |
| 3,436,170 | 4/1969 | Lodge | 21/94 X |
| 3,454,352 | 7/1969 | Lamboy et al. | 21/103 X |
| 3,454,353 | 7/1969 | Bjork | 21/103 X |
| 3,479,131 | 11/1969 | Scoffield et al. | 21/103 |

FOREIGN PATENTS OR APPLICATIONS

| | | | |
|---|---|---|---|
| 267,073 | 12/1968 | Austria | 21/98 |

*Primary Examiner*—Morris O. Wolk
*Assistant Examiner*—Bradley R. Garris
*Attorney, Agent, or Firm*—Theodore B. Roessel; Roger Aceto

[57] ABSTRACT

Steam and entrapped air are bled from a steam sterilizing chamber and into a water displacement tube. The steam component of the bleed is condensed in the tube while any air entrapped in the steam displaces water from the tube. As the water level in the tube drops to a predetermined level, the tube is vented and the sterilizing chamber is pulse vented to introduce additional steam into the chamber. The method contemplates delaying the start of the sterilization period until a sufficiently low amount of air remains in the sterilizing chamber as determined by the intervals between repeated venting of the tube exceeding a predetermined timed interval.

8 Claims, 2 Drawing Figures

METHOD AND APPARATUS FOR DETECTING ENTRAPPED AIR IN A STEAM STERILIZER

BACKGROUND OF THE INVENTION

The present invention relates generally to steam sterilization and more specifically to a method and apparatus for more effectively controlling and monitoring the amount of residual air in the sterilizing chamber.

It is known that in a steam sterilization process, a saturated steam condition produces the best biocidal kill. Both air entrapment, that is, residual air in the sterilizer chamber, and super heat conditions within the sterilizer result in an unsaturated steam condition, and therefore, a decreased biocidal kill or sterilization rate. For example, a super heat condition within the chamber can result in a premature actuation of various thermal sensing devices which initiate a timed sterilization period. It is known that a moderate amount of super heat, say between 5° to 10°F, results in an insignificant change in the effectiveness of the sterilization process. Compensating for the effects of super heat within this range is easily accomplished by the prudent placement of the thermal sensing devices within the sterilizing chamber or otherwise protecting the devices so that there is a delay in the sensing of the super heat condition.

It is most desirable to control and monitor the steam sterilizer chamber conditions with pressure operated devices. This is because the chamber pressure is equal throughout and consequently a pressure sensing device does not have to be prudently placed to avoid being actuated by super heat. Further, pressure devices do not exhibit the large thermal lag of temperature sensing devices and such devices are much easier to calibrate and maintain. However, the primary drawback of pressure operated devices, is that the proper operation of such devices in a steam sterilization process is contingent upon the adequate removal of air from the chamber.

Residual or entrapped air in the sterilizing chamber results in the inaccurate operation of the pressure operated controllers and/or indicators in the sterilizer due to the effects of the partial pressure of air. The biological effects of air entrapment also have been reported to be noticeable when the amount of air within the sterilizing chamber exceeds about 1% by volume. While the problem of super heat can be overcome as discussed above, the amount of air remaining in the sterilizer chamber is not readily measurable by pressure-temperature correlation and should the amount of residual air exceed 1 percent, the resulting air and steam condition could adversely effect the sterilization process.

The method and apparatus of the present invention provides for a continuous sampling of the environment within the sterilizing chamber to test for residual air and then initiating the timed sterilizing cycle when the residual air has reached a predetermined low limit. During the sterilizing cycle, the readings of any pressure sensors within the chamber are thus more accurate as there is no correction necessary due to the partial pressure of air within the chamber.

SUMMARY OF THE PRESENT INVENTION

The present invention may be characterized in one aspect thereof by the provision of a water displacement tube in communication with the sterilizing vessel, the tube having a valved vent; a water level sensor in the tube; and control means acting responsive to the water level sensor to cycle the valved vent open and closed and to pulse vent the sterilizing chamber. Steam from the sterilizing chamber together with entrapped air is continuously bled into the water displacement tube until such time as the interval between the cycling of the valved vent exceeds a predetermined time period, the control means thereafter initiate a timed sterilizing period.

OBJECTS OF THE INVENTION

One object of the present invention is to provide a simple, efficient air entrapment indicator for steam sterilizers and the like.

Another object of the present invention is to provide a method and apparatus for continuously monitoring the environment within the steam sterilizer in order to detect any excessive amounts of residual air therein.

A further object of the present invention is to provide a means for initiating a timed steam sterilizing period after the residual air within the sterilizing chamber has reached a predetermined low level.

Yet another object of the present invention is to provide means for greatly reducing the amount of residual air in the steam sterilizing chamber so as to permit the sterilizer control mechanisms to be pressure actuated with a high degree of confidence that the measured conditions are those for saturated steam.

Still another object is to provide an air entrapment indication which can abort a steam sterilizing cycle whenever excessive amounts of air are detected in the sterilizing chamber during the sterilization period.

These and other objects, advantages and characterizing features will become more apparent upon consideration of the following detailed description of the invention when taken in connection with the accompanying drawings depicting the same.

DESCRIPTION OF THE PREFERRED EMBODIMENT

Figure 1:
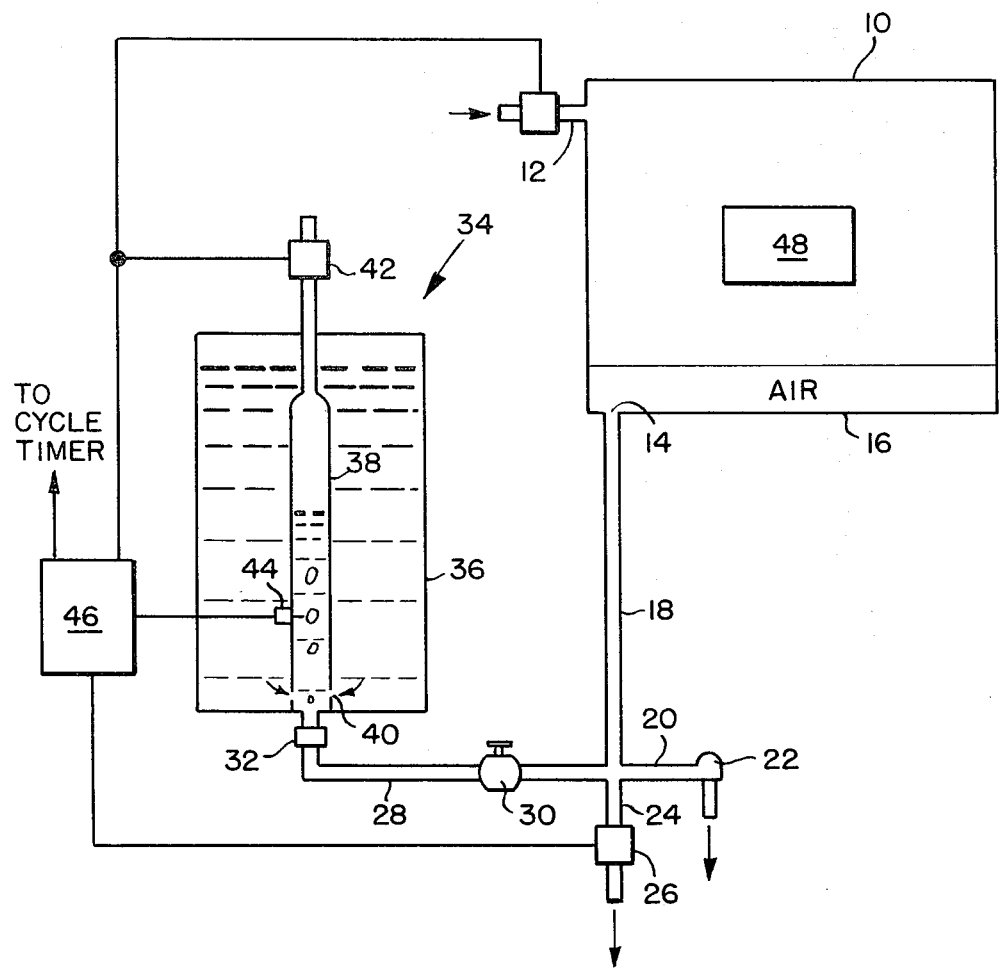
FIG. 1 is a schematic representation of the air entrapment indicator and controller of the present invention.

Referring to the drawings, FIG. 1 shows a steam sterilizing chamber 10 having a valved steam inlet 12 and a drain 14. As steam is introduced through inlet 12 the air which is heavier than steam tends to stratify at the bottom of the chamber and is displaced downward and out through drain 14. Preferably, the bottom 16 of the sterilizing chamber has a continuous negative slope to the lower point of the chamber where drain 14 is located. As a practical matter there is some mixing of the steam and air so that while air may initially move through drain 14, an air-steam mixture will eventually pass through the drain with the air component gradually diminishing.

Drain 14 is connected to a drain line 18 which in turn has three branches. A first branch 20 includes an air trap bellows assembly 22. Such an air trap is well known in the art and it is sufficient for purposes of the present invention, merely to say that the steam and air being vented from the chamber passes through this conventional air trap bellows until the majority of air has been removed from the chamber, at which time the bellows assembly closes. In a conventional steam sterilizer, the introduction of steam continues after the bellows is closed so as to build up the pressure within the sterilizing chamber.

The second branch 24 of the drain line has a valve 26 for opening and closing the drain line for purposes set out hereinbelow. The third branch 28 contains a pressure regulator 30 and a metering orifice 32. This third branch 28 is connected to a water displacement tube assembly generally indicated at 34.

The assembly includes a displacement tube 38 disposed within a water reservoir 36, the tube being in communication with the third branch 28 of the drain line. Displacement tube 38 has several openings 40 adjacent its lower end to permit the free flow of water from reservoir 36 into the displacement tube. The top of the displacement tube can be vented to atmosphere through a valved exhaust line 42. Any conventional level sensor 44 is located at a predetermined position within tube 38 for issuing an electrical signal whenever the water level within the tube falls below the sensor. While the tube can be located outside of the reservoir, the arrangement as shown, helps to cool the tube and condense the steam as set out hereinbelow.

Completing the invention is a control means 46 which receives the electric signal from level sensor 44 and in response thereto issues various command signals to open or close the various valves including valved steam inlet 12, valve 26 and valved exhaust 42.

In operation, the goods 48 to be steamed sterilized are loaded into and sealed within sterilizing chamber 10. Valved steam inlet 12 is then opened to introduce steam into the sterilizing chamber. Air within the chamber is displaced downwardly through drain 14, drain line 18, first branch 20 and through the air trap bellows assembly 22 to atmosphere. After the majority of the air has been removed, bellows assembly 22 closes and the chamber pressure then increases as steam continues to be introduced into the chamber. The increasing chamber pressure permits an air-steam mixture to flow through pressure regulator 30 and a metering orifice 32 into water displacement tube 38. As the steam constituent comes into contact with the water in the displacement tube, it condenses. The air constituent of the mixture rises in tube 38 and displaces water from the tube through openings 40 and into water reservoir 36. As the water level within the displacement tube 38 falls below level sensor 44, the level sensor will issue an appropriate signal to controller 46. The controller, in turn, will cause both valve 26 and the valved exhaust 42 to open. Opening valve 26 (with or without opening valved steam inlet 12) allows a pulse venting of the chamber so that an amount of the air-steam mixture is vented from the sterilizing chamber. Opening valved exhaust 42 allows the air to escape from water displacement tube 38. This in turn permits the water to flow back from the reservoir through openings 40 and into the water displacement tube. Controller 46 then closes valve 26 and valved exhaust 42 and the entire process is repeated.

The repetitions continue until such time as substantially all the air is removed from the chamber as evidenced by the failure of the water level in the displacement tube to fall below level sensor 44 at which time controller 46 issues the signal to begin a timed sterilization cycle.

During the timed sterilization cycle and as load 48 becomes heated, air within the load expands and is diffused out of the load. This residual air not only seeks the bottom of the chamber in the same fashion as the initial air-steam mixture, but also diffuses throughout the chamber. In any event, residual air passing from the chamber through drain 14 causes the water level within the displacement tube 38 to drop. At such time as the water level falls below sensor 44, the sterilizing chamber is again pulse vented (with the opening of valved steam inlet 12) so as to remove the air at the chamber bottom and reduce the overall air content of the chamber by delution.

To insure that the timed sterilization period does not begin until after substantially all of the air has been removed from the chamber, controller 46 may include a delay timer to indicate the time interval between successive openings of valved exhause 42 and/or the pulse venting of the sterilizing chamber. In this respect, such time interval increases as the air content of the sterilizing chamber decreases. As a result, the initiation of the timed sterilization period can begin after such time interval exceeds a predetermined timed interval representative of an acceptable low air level in the sterilizing chamber. In this case, then, the time interval and the level of water in the tube determine when the timed sterilization period starts.

Figure 2:
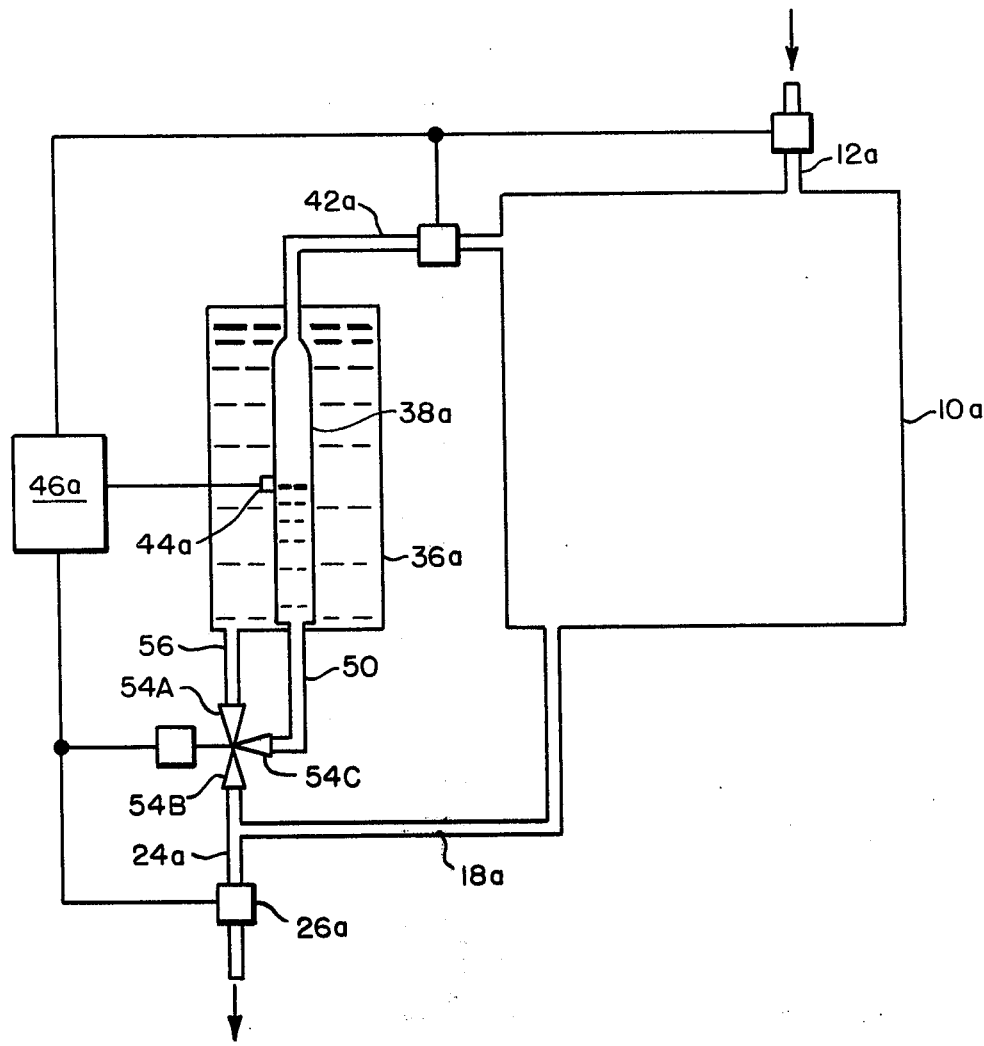
FIG. 2 shows another embodiment of the invention.

A modified version of the air entrapment indicator is shown in FIG. 2. For purposes of description structure in FIG. 2 similar to structure in FIG. 1 is identified by the same reference numeral with the suffix (a).

FIG. 2 shows the sterilizing chamber 10a, water displacement tube 38a and water reservoir 36a. In this embodiment valved exhaust 42a connects the top of the water displacement tube directly to the sterilizing chamber. Extending from the bottom of the water displacement tube and through the reservoir is a line 50. This line connects the tube to one port 54C of a three-way valve. Another port 54B of the valve is connected via branch line 24a and drain line 18a to the bottom of the sterilizer chamber. Completing the structure is yet another line 56 which connects the bottom of the reservoir to valve port 54A.

From the drawing it can be appreciated that when valved exhaust line 42a is open and valve ports 54C and 54B communicate, water displacement tube 38a is in direct communication with chamber 10a. Steam and air enter the tube from the sterilizing chamber so that the tube contains an air/steam mixture which by volume proportionately approximates the air/steam ratio within the sterilizing chamber.

Since the walls of the tube are cooled by the reservoir water, steam within the tube is condensed and the resulting water drains out by gravity through line 50, ports 54C and B, branch line 24a and valve 26a. The condensation of steam in the tube results in a steam and air migration to fill the void so that more steam and air enter the tube from the sterilizing chamber. This continues for a predetermined timed period so that a relatively small tube 38a can be made to sample a relatively large volume of steam. Then, at a given time, controller 46a cycles valved exhaust 42a close and puts valve ports 54A and 54C of the valve into communication. This allows water from the reservoir to enter the tube to collapse any steam remaining in the collection tube. The air in the tube now can be measured directly from the water column height. Should the water level in the tube be below sensor 44a, the controller will operate to restore the communication between port 54C and 54B, and open valved exhaust line 42a, valve 26A and steam inlet 12A. This allows the collapsed steam within the water displacement tube to gravity feed out of the tube while at the same time, pulse venting the sterilizer chamber. The pulse venting of the sterilizer chamber will also tend to push air out of the displacement tube through lines 50 and 24a. A vacuum pump (not shown) connected to line 24A can assist in the evacuation of air and water from the displacement tube and also in the pulse venting of the sterilizing chamber. Controller 46a would then operate to restore the initial position of the valves that is, open valve exhaust line 42a and put ports 54C and 54B in communication so that a representative sample of the steam/air mixture is again present in the displacement tube. The above procedure is repeated until such time as the water level created by the collapsing steam remains above sensor 44a. At this point, controller 46a would initiate the timed sterilization period.

Thus, it should be appreciated that the present invention accomplishes its intended objects in providing a simple efficient and accurate air entrapment indicator for initiating the timed sterilization period immediately after substantially all of the air has been removed from the sterilizing chamber. The present invention not only is capable of continuously monitoring the environment of a steam sterilizer, but also lends itself to a means for aborting the sterilizing cycle should a leak or other situation result in air entering the sterilizing chamber before the end of the sterilizing period. In this event, any time the water level falls to level sensor 44 (FIG. 1) during the timed sterilization period, controller 46 will issue a signal immediately terminating the sterilizing cycle.

Rather than having the water tube displacement tube 38 sampling only a portion of the vented air-steam mixture, it is well within the skill of the art to vent the entire contents of the sterilizer through the water displacement tube assembly. This would require simply connecting vent line 18 directly to water displacement tube 38. It is also possible to remove a portion of the air with a vacuum pump at some time or another but this is not suitable for all types of goods to be sterilized.

Having thus described the invention in detail, what is claimed as new is:

1. Method for detecting entrapped air in a steam sterilizer wherein steam is introduced into a sterilizing chamber to displace the air therefrom, comprising the steps of:
   a. conducting an air-steam mixture from said chamber and into a water displacement tube wherein the steam component of said mixture condenses while the air entrapped in said mixture displaces water from said tube;
   b. sensing the level of water in said displacement tube;
   c. venting said chamber responsive to the level of water in said tube falling below a predetermined level; and
   d. venting air from said tube to permit refilling of said tube with water.

2. A method as in claim 1 comprising:
   e. repeating steps (a) to (d) until the water level in said tube remains above said predetermined level; and thereafter
   f. initiating a timed sterilization period.

3. A method as in claim 1 comprising:
   e. repeating steps (a) to (d); and thereafter
   f. initiating a timed sterilization period when the time between successive repetitions exceeds a predetermined time interval.

4. A method as in claim 1 wherein step (a) continues during a timed sterilization period, said sterilizer chamber being vented each time the water level in said water displacement tube falls below said predetermined level.

5. A method as in claim 1 wherein steam is introduced into said chamber during said chamber venting step.

6. An air entrapment indicator for steam sterilizing apparatus having a sterilizing chamber provided with a valved steam inlet and a valved drain, said indicator comprising:
   a. an upright water displacement tube having a valved exhaust in the upper portion thereof;
   b. means for introducing a mixture of air and steam from the sterilizing chamber into said tube, the steam in said mixture condensing in said tube and the air in said mixture displacing water from said tube;
   c. a level sensor for issuing a signal when the water level in said tube falls below a predetermined level; and
   d. control means operating responsive to a signal from said level sensor to open said valved exhaust, said control means being adapted to open the valved steam inlet and valved drain of the sterilizing chamber to pulse vent said chamber.

7. An air entrapment indicator as in claim 6 including a water reservoir in communication with said water displacement tube.

8. An air entrapment indicator as in claim 7 wherein said water displacement tube is located in said water reservoir, said tube being in open communication adjacent its bottom with said water reservoir.

* * * * *